United States Patent [19]

Marple et al.

[11] Patent Number: 4,827,779
[45] Date of Patent: May 9, 1989

[54] CARTRIDGE PERSONAL SAMPLING IMPACTOR

[75] Inventors: Virgil A. Marple, Maple Plain; Benjamin Y. H. Liu, North Oaks, both of Minn.

[73] Assignee: Regents of the University of Minnesota, Minneapolis, Minn.

[21] Appl. No.: 185,159

[22] Filed: Apr. 22, 1988

[51] Int. Cl.⁴ .............................................. G01N 1/24
[52] U.S. Cl. ............................. 73/863.22; 73/863.25; 73/864.71
[58] Field of Search ........... 73/863.22, 863.23, 863.24, 73/863.25, 864.71

[56] References Cited

U.S. PATENT DOCUMENTS

| | | | |
|---|---|---|---|
| 3,957,469 | 5/1976 | Nebash | 55/270 |
| 3,966,439 | 6/1976 | Vennos | 73/863.22 |
| 4,159,635 | 7/1979 | Sehmel | 73/863.22 |
| 4,586,389 | 5/1986 | Vincent et al. | 73/863.22 |
| 4,640,140 | 2/1987 | Burghoffer et al. | 73/863.22 |
| 4,740,220 | 4/1988 | Mark et al. | 73/863.22 X |

Primary Examiner—Tom Noland
Attorney, Agent, or Firm—Kinney & Lange

[57] ABSTRACT

A personal sampling impactor that comprises a compact mounting arrangement using a base, a cover, and an impactor plate cartridge that fits within the cover and is supported on an upper end of the base. A filter is held in place between the impact plate cartridge and the base, and the cover is made so that it can easily be placed over the impaction plate and latched in place to hold the unit together. The cover has inlets that align with a lightly oiled impaction plate surface on which particles will adhere.

8 Claims, 2 Drawing Sheets

AIR PUMP

CARTRIDGE PERSONAL SAMPLING IMPACTOR

BACKGROUND OF THE INVENTION

1. Field of the Invention

The present invention relates to small ambient air sampling impactors that are capable of being worn by a person.

2. Description of the Prior Art

Small filter cassette type samplers have been advanced in the art, and a typical one is shown in U.S. Pat. No. 3,957,469 which shows a two-part cassette that holds a capsule clamped between the two parts. However, the overall assembly of the cassette is rather complex and uses a recess type compaction plate. The attachments for this compaction plate also require special fittings or posts and thus the structure is more complex than the simple, compact, easily used impactor of the present invention.

SUMMARY OF THE INVENTION

The present invention relates to a personal impactor that is very simply made, and uses a universal base for different types of impactor plates and inlets. The impactor is designed to retain the filter and impactor plate assembly underneath a cover that is attached to the base to form a housing, and air is drawn through the housing from a pump attached to an outlet leading from the base.

The base is an open top cup-shaped member that supports a filter across its open top. The impactor plate is a flat wall supported by a peripheral rim type wall that spaces the impactor plat from the filter. The edges of the rim type wall opposite from the impactor plate rests on the filter to hold it in place. The impactor plate and peripheral rim type wall form a cartridge. The impactor plate cartridge and the filter are held in assembly with the cover member that fastens to the base.

Two forms of the impactor are utilized, one with a centrally located impactor plate, with air passages out near the outer periphery of the cartridge, and a second form of the cartridge has an impactor plate section around the outer periphery, with an air passage to the base in the center of the impactor plate. The housing parts are easily put together, and easily disassembled for inspection, counting of collected particles, cleaning and other servicing. BRIEF DESCRIPTION OF THE DRAWINGS FIG. 1 is a top plan view of a personal impactor made according to the present invention;

DETAILED DESCRIPTION OF THE PREFERRED EMBODIMENTS

Figure 1:
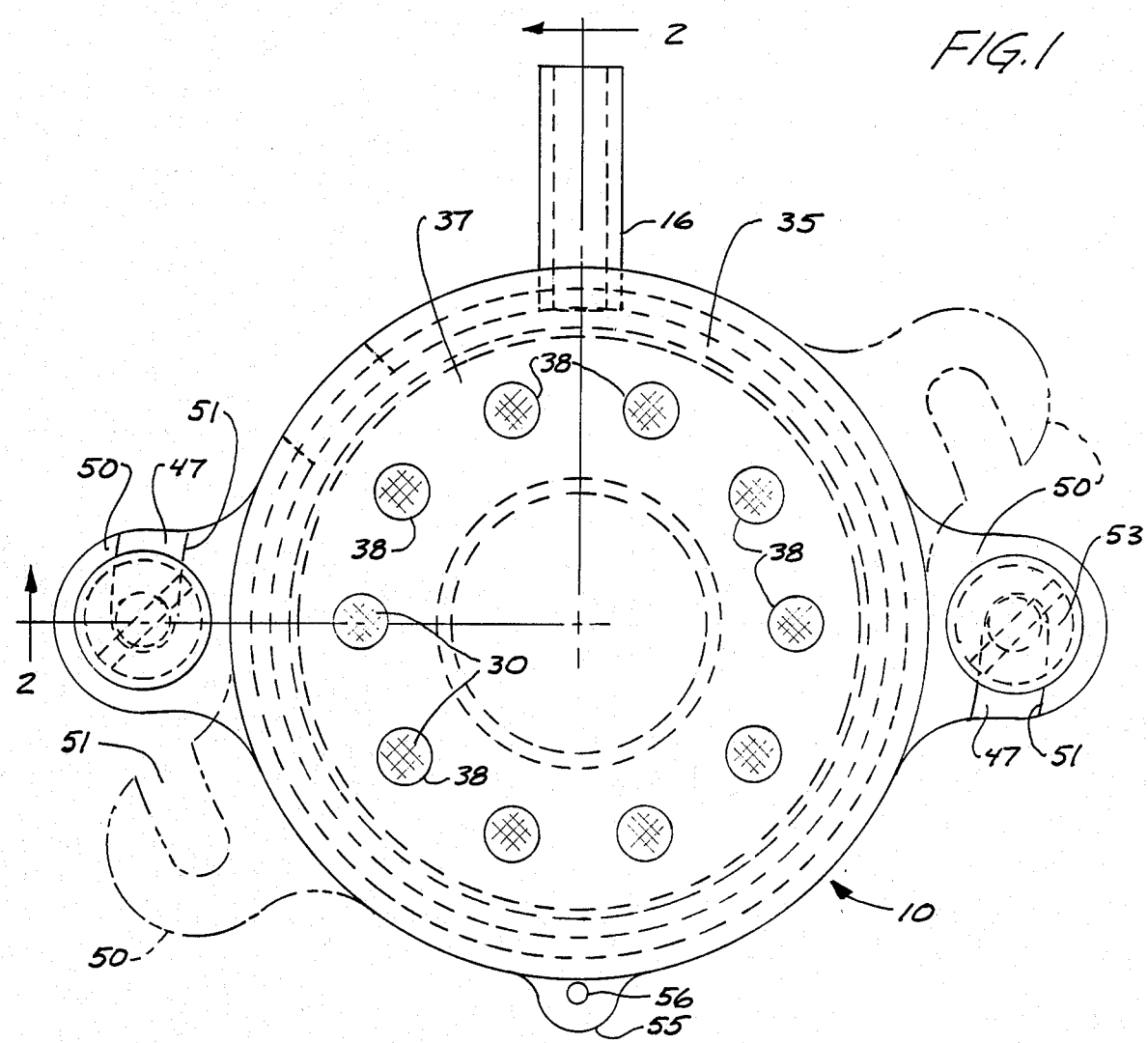

A personal sampling impactor assembly 10 comprises a base 11, which includes a bottom wall 12 and an annular peripheral wall 13. The peripheral wall 13 forms an open top cup member forming a chamber 15. The peripheral wall 13 has an internal shoulder 14 formed at the open top. The chamber 15 has an air conduit 16 open thereto and the conduit is in turn coupled to an air pump 17 on the exterior that provides a desired volume of flow from the chamber 15, through the conduit 16.

The shoulder 14 is of size to receive and support a filter assembly 20 of conventional design which is useful for collecting particles as air passes through it. Filter assembly 20 has a peripheral shape that corresponds to the peripheral shape of the shoulder 14. As shown, peripheral wall 13 is cylindrical, so that the outer edge of the filter 20 forms a circle.

An impactor plate cartridge 22 is supported on the top of the filter, and is defined by a peripheral wall 23 that is of slightly smaller size than the periphery of the wall 13, and is substantially the same peripheral size as the filter assembly 20. The impactor plate cartridge wall 23 has an end peripheral edge 26 supported on top of the filter assembly 20 on the shoulder 14. The wall 23 forms a chamber 24 in connection with an impactor plate support wall 25 which joins the wall 23 at the opposite end thereof from the filter assembly 20.

The impactor plate support wall 25 has, in this form of the invention, an annular ring type (peripheral) recess that supports a porous material layer insert indicated at 30, that can be lightly oiled, and to which particles striking the surface of this insert will adhere. The porous material is the particle collection material arranged in an annular ring on the upper surface of the impactor cartridge 22.

The wall 25 also has a central opening 31 of substantial size through which air can flow.

The cartridge 22 and the filter 20 are retained in place through the use of a cover assembly 35 which has an annular peripheral wall 36 that fits to the exterior of the wall 23 of the impactor cartridge 22. The cover assembly 35 has a top wall 37 joining the peripheral wall 36 with a plurality of apertures 38 therethrough that are arranged around the central axis of the cover so that the openings 38 directly align with the insert of porous material 30 that is the particle collection material. The cover 35 and base 11 form a housing when assembled together.

The wall 36 is of sufficient axial height so that there is a plenum chamber 40 formed between the cover top wall 37 and the upper surface 30A of the insert of porous particle retaining material 30. In the form of the invention shown in FIGS. 1 and 2, there is a shoulder 41 that will engage the upper surface of the impactor cartridge 22, so that the cartridge 22 will be forced against the filter and held in place by the cover. If desired, suitable resilient material can be positioned between the shoulder 41 and the cartridge 22 to form a gasket to hold the cartridge in place. The cartridge 22 holds the filter assembly 20 in its position during use. The lower edge of the cover is spaced slightly from the base 11.

When the air pump 17 is operating, air will flow into the housing as indicated by the arrow 45, (FIG. 2) and airborne particles will strike the upper surface 30A of the porous material 30 at a location indicated at 30B. The air will flow through the opening 31, and out through the filter assembly 20 in chamber 15, and then through the conduit 16 to the air pump, which will discharge the air into the atmosphere or through a secondary filter if desired.

Large particles will tend to be collected on surface 30A by adhering to the oiled surface. Smaller particles will not strike surface 30A but will pass through the opening 31 and be collected on the filter assembly 20.

Figure 2:
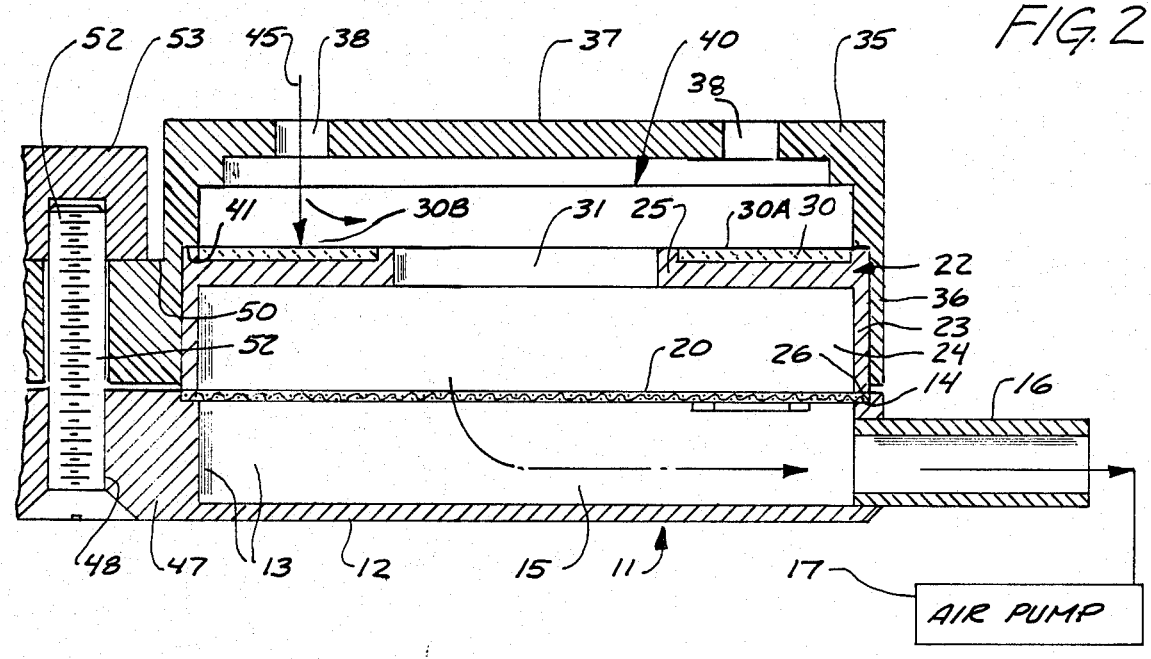
FIG. 2 is a sectional view taken on line 2—2 in FIG. 1.

In order to secure the cover 35 to the base 11, the base 11 has a pair of ears 47,47 on diametrically opposite sides thereof, which are fixed to base 11. The ears 47 each have an opening 48 therein. The cover 35 has a pair of mating ears 50 thereon, which also are diametrically opposed, as shown in FIG. 1, and these ears 50 have open slots 51 that have their open ends facing in the same rotational direction. A screw 52 is mounted in each of the openings 48 and extends upwardly above ears 47. A threaded cap or nut 53 is placed on each of the cap screws and enough room is left for the ears 50 to fit under the caps or nuts 53. The cover 35 can be put into position with the ears 50 in location as shown in dotted lines in FIG. 1, and with the nuts or caps 53 sufficiently loosened, the cover 35 can be rotated so that the slots 51 will fit around the shanks of the screws 52. Then the nuts or caps 53 can be tightened down to clamp the cover 35 in place so that the ears 47 and 50 are in registry and held together.

The cover 35 can easily be removed by slightly loosening the nuts or caps 53, which will only be hand tightened, and then rotating the cover 35 in counterclockwise direction as shown in FIG. 1 to release the cover.

The base 11 has a small tab 55 thereon with an opening 56 that can be used for hanging the impactor unit from a user's belt, or otherwise fastening it onto a user.

Figure 3:
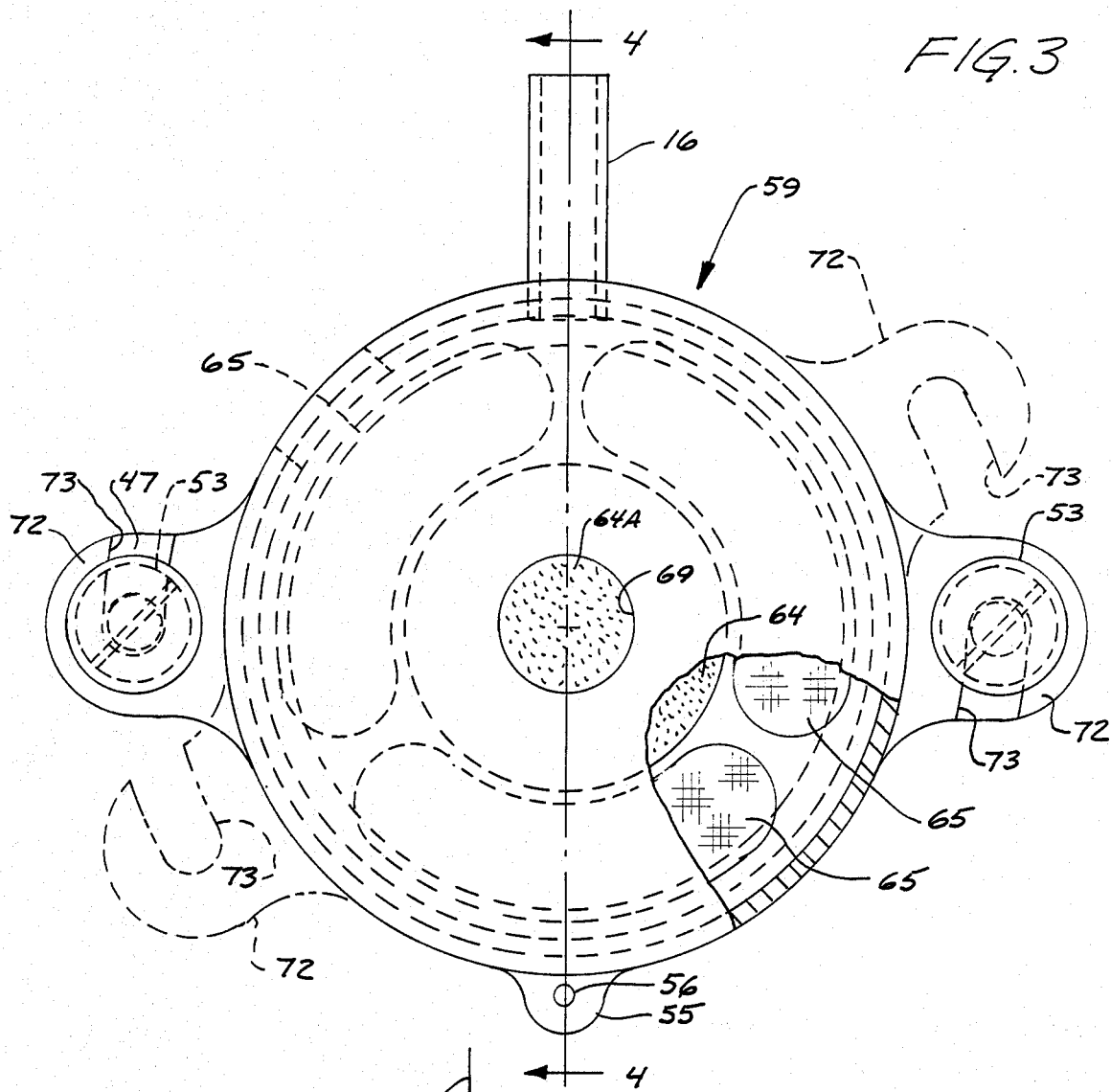
FIG. 3 is a top plan view of a modified form of the present invention.
Figure 4:
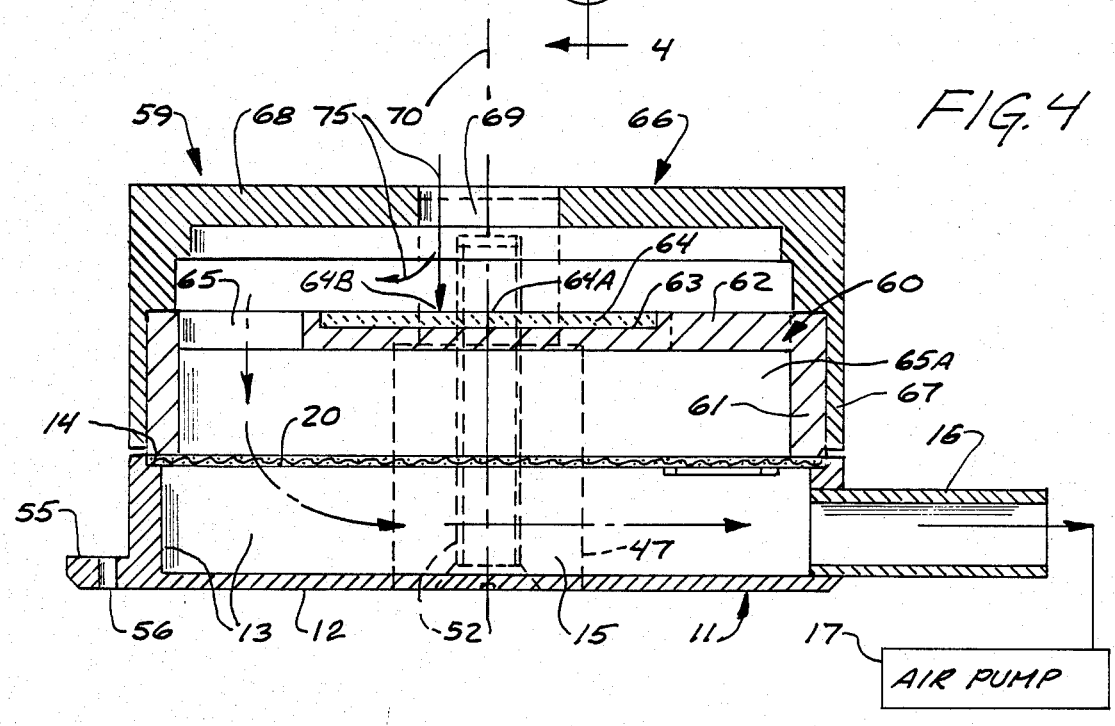
FIG. 4 is a sectional view taken as on line 4—4 in FIG. 3.

The impactor assembly is thus very compact, and as will be seen in connection with FIGS. 3 and 4, different types of covers and cartridges can be utilized with substantially the same base. The assembly is easily serviced because the cover 35 can be removed quickly, and the filter assembly 20 and impactor cartridge 22 are easily retained by the cover in a proper position for receiving impinging particles that pass through openings 38.

In a second form of the invention shown in FIGS. 3 and 4, the same base 11 is utilized, and it has the bottom wall 12 and the peripheral wall 13 forming a chamber 15 as previously explained. It also includes the same cover retainer ears 47 and mounting arrangement. A filter assembly 20 is positioned on the shoulder 14 as in the previous form of the invention, and in this case, a personal sampling impactor 59 includes an impactor cartridge 60 that has a peripheral wall 61 which fits over the filter assembly 20 in the same manner as the peripheral wall 23 of the previous cartridge, The impactor cartridge 60 has a top wall 62 that is joined to the wall 61. The cartridge 60 thus is an inverted cup shape having a peripheral wall 61 and a base top wall 62. In this form of the invention, the top wall 62 is provided with a recess 63 for mounting an insert of porous material 64, which insert forms a particle collection material.

There are three arcuate or generally kidney-shaped openings 65 positioned around the periphery of the impactor collection material 64 and passing through the wall 62. As can be seen in FIG. 3 as well as in FIG. 4, these openings 65 provide passageways for air flow that will be created through the personal sampling impactor.

A cover member 66 has a peripheral wall 67 that surrounds the wall 61, and overlies and is slightly spaced from the wall 13 of the base 11. The cover member 66 has a cover wall 68 forming an inverted cup-shaped cover that surrounds and retains the particle impactor cartridge 60 in place by clamping the cartridge against the base 11. The wall 68 has a central or axial opening 69 therethrough which is centered on the central axis 70 of the personal impactor. The opening 68 is positioned to overlie the centrally located insert 64 of porous particle collection material. The cover 66 also has ears 72 thereon which correspond in size and position to the ears 50, and which have slots 73 that fit over the screws 52, so that the nuts 53 can be tightened down as in the previous form of the invention to secure the cover 66 in place. The cover 67 can be removed by turning it counterclockwise as shown previously, for easy removal and replacement of the cartridge 60 and inspection of the insert of porous particle collection material 64.

The air flow established by the air pump 17 is through the opening 69, as indicated by the arrows 75 (FIG. 4), and particles will strike the upper surface 64A of the insert of particle collection material 64 as indicated by the location at 64B. Large particles will be collected on surface 64A while smaller particles will not stick on surface 64A, but will pass through the opening 65 and be carried with the air into the chamber 65A which is defined by the wall 61, and then to the filter assembly 20. The air flows out through chamber 15, conduit 16 and into the air pump 17 as previously explained.

This arrangement of the impactor cartridge on a base and using a cover having the air inlet opening provides for a compact impactor that can easily be inspected for determining what particles have been collected, and which can be easily taken apart and put together for service such as cleaning, reoiling of the insert of porous particle collection material 64, and even for replacement of the cover and particle collection cartridge, if desired.

Although the present invention has been described with reference to preferred embodiments, workers skilled in the art will recognize that changes may be made in form and detail without departing from the spirit and scope of the invention.

What is claimed is:

1. A personal sampling impactor for sampling aerosols from the atmosphere comprising a base having a peripheral wall defining a chamber, said base having a base wall joining the peripheral wall to close one end of the chamber and define an open top;
    means at the open top for supporting a filter;
    a filter supported on said means for supporting;
    an impaction plate cartridge comprising a second peripheral wall having substantially the same shape as the base, and being of slightly smaller lateral size than the base to thereby nest in the base, and an impaction plate support wall joining the second peripheral wall and being supported to overlie the filter and be spaced therefrom when the second peripheral wall is mounted over the open end of the base and resting on the filter, said impaction plate support wall including impaction plate means thereon and having at least one perforation therethrough for permitting air passage therethrough;
    an inlet cover defining a third preipheral wall having an inner surface of a size to fit around the second peripheral wall of the impaction plate cartridge, said cover member having an outer end wall joining the third peripheral wall, said impaction cover having inlet means therein for air flow therethrough;
    means for holding the cover on the base with the impaction plate cartridge within the cover and supported on the base; and
    means for permitting withdrawal of air from the base to establish a flow through the inlet opening, through the impaction plate cartridge, through the filter and out through the means for permitting withdrawal.

2. The apparatus as specified in claim 1 including a means for releasably securing a cover directly on the base comprising at least one pair of ears fixed to said base and extending outwardly therefrom, a pair of mating ears on the cover, said mating ears having slots therein of size to receive threaded members mounted in said ears, and the slots being oriented so that upon twisting the cover the slots will be moved to engage the threadable means.

3. The apparatus of claim 1 wherein said impaction plate support wall has a perforation on a central axis thereof, and said impaction plate means surround the opening and form an annular band therearound.

4. The appparatus as specified in claim 1 wherein said impaction plate support wall has a central solid portion, said impaction plate means being mounted in a central portion, and the at least one perforation comprises a part annular opening to the outside of said impaction plate means and positioned between the impaction plate means and the support wall of the impaction plate cartridge.

5. The apparatus as specified in claim 1 comprising a pair of impaction plate cartridges which are interchangeably fittable within the inlet cover, said impaction plate cartridges comprising the first mentioned impaction plate cartridge wherein the impaction plate support wall has an opening in the center portion thereof, and the impaction plate means is mounted to surround said opening in a substantially annular band, and a second impaction plate cartridge having a second cartridge impaction plate support wall that has an aperture near the outer periphery thereof, and having second cartiridge impaction plate means mounted in the central portions of the second cartridge impaction plate suport wall.

6. A personal sampling impactor comprising:
a base forming a cup shape, a filter supported on said base across an open top thereof, and a cover member mounted on said base to define an interior chamber;
inlet means in said cover for providing an air inlet, and an air outlet from said base whereby the air passes across the filter;
impaction plate means mounted within said cover and spaced from said filter, said impaction plate means comprising a plate having at least one aperture therethrough for permitting air flow, and a section of said impaction plate means having an impaction plate surface that is offset laterally from the aperture, said impaction plate surface being aligned with the air inlet in the cover;
the base and cover having a minimum size for providing a flow of air so that the cover can be mounted on a person for sampling air; and
means for removably mounting the cover on said base comprising a pair of ears on the base having cap screw means extending therethrough and being spaced from the outer periphery of the cover, said cover having a pair of ears that mate with the ears on the base and have slots for receiving the cap screws upon a rotary motion of the cover relative to the base to provide a quick attachment feature for the cover.

7. The apparatus as specified in claim 6 wherein said impaction plate means comprises an impaction plate cartridge having a peripheral wall, and an impaction plate support wall joining the peripheral wall to extend across one end of the peripheral wall, said impaction plate support wall comprising a wall having an opening and the impaction plate means mounted thereon, said cartridge being removable from the base when the cover is removed and being retained relative to the base when the cover is in place on the base.

8. The apparatus as specified in claim 7 where impaction means comprises a porous material that will retain a coating of oil thereon.

* * * * *

UNITED STATES PATENT AND TRADEMARK OFFICE
CERTIFICATE OF CORRECTION

PATENT NO. : 4,827,779

DATED     : May 9, 1989

INVENTOR(S) : Virgil A. Marple et al

It is certified that error appears in the above-identified patent and that said Letters Patent is hereby corrected as shown below:

Column 4, line 54, delete "preipheral", insert --peripheral--.

Column 5, line 33, delete "cartiridge", insert --cartridqe--.

Column 5, line 35, delete "suport", insert --support--.

Signed and Sealed this

Ninth Day of January, 1990

*Attest:*

JEFFREY M. SAMUELS

*Attesting Officer*    *Acting Commissioner of Patents and Trademarks*